(12) United States Patent
Fuerst et al.

(10) Patent No.: US 8,394,014 B2
(45) Date of Patent: Mar. 12, 2013

(54) ENDOSCOPE

(75) Inventors: Frank Fuerst, Tuttlingen (DE); Joerg Halbig, Constance (DE); Markus Kupferschmid, Emmingen-Liptingen (DE); Fang Lei, Durchhausen (DE); Sven Mersmann, Tuttlingen (DE); Jan Dahmen, Seitingen-Oberflacht (DE); Ewald Stihl, Geisingen (DE); Frank Lederer, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 941 days.

(21) Appl. No.: 11/550,697

(22) Filed: Oct. 18, 2006

(65) Prior Publication Data

US 2007/0118014 A1 May 24, 2007

(30) Foreign Application Priority Data

Oct. 18, 2005 (DE) .................. 10 2005 051 209

(51) Int. Cl.
*A61B 1/04* (2006.01)
*A61B 1/00* (2006.01)
*A61B 1/06* (2006.01)

(52) U.S. Cl. ......... 600/130; 600/123; 600/153; 600/182

(58) Field of Classification Search ............... 600/108, 600/123, 130, 153, 182, 140, 175, 114, 160, 600/121–122, 124–125; 604/160, 161
See application file for complete search history.

(56) References Cited

U.S. PATENT DOCUMENTS

| 3,261,350 | A | * | 7/1966 | Wallace ............... 600/182 |
| 3,297,022 | A | * | 1/1967 | Wallace ............... 600/172 |
| 3,498,286 | A | * | 3/1970 | Koester et al. ......... 600/325 |
| 4,601,713 | A | * | 7/1986 | Fuqua ................ 604/514 |
| 4,790,295 | A |   | 12/1988 | Tashiro ................ 128/6 |
| 4,921,479 | A | * | 5/1990 | Grayzel ............... 604/509 |
| 5,051,824 | A | * | 9/1991 | Nishigaki ............. 348/68 |

(Continued)

FOREIGN PATENT DOCUMENTS

DE 199 28 289 A1 1/2001
DE 103 07 903 A1 9/2004

(Continued)

OTHER PUBLICATIONS

European Search Report, Jan. 12, 2007, 6 pages.

(Continued)

*Primary Examiner* — Alireza Nia
(74) *Attorney, Agent, or Firm* — St. Onge Steward Johnston & Reens LLC

(57) ABSTRACT

An endoscope comprises a shaft with an outer tube and with an inner tube extending inside the latter, the outer and inner tubes being radially spaced apart from one another such that they form between them an axially extending channel, which provides space for receiving a light guide. An intermediate tube having flexural strength is arranged between the outer tube and the inner tube, which intermediate tube at least partially surrounds the inner tube.

6 Claims, 4 Drawing Sheets

U.S. PATENT DOCUMENTS

| | | | | |
|---|---|---|---|---|
| 5,201,756 A * | 4/1993 | Horzewski et al. | 606/198 |
| 5,217,456 A * | 6/1993 | Narciso, Jr. | 606/15 |
| 5,318,526 A * | 6/1994 | Cohen | 604/95.04 |
| 5,322,512 A * | 6/1994 | Mohiuddin | 604/160 |
| 5,456,245 A * | 10/1995 | Bornhop et al. | 600/139 |
| 5,591,120 A * | 1/1997 | Machida et al. | 600/140 |
| 5,700,236 A * | 12/1997 | Sauer et al. | 600/175 |
| 5,735,792 A | 4/1998 | Vanden Hoek et al. | 600/138 |
| 6,527,707 B1 | 3/2003 | Frische et al. | 600/153 |
| 7,077,836 B2 * | 7/2006 | Lary et al. | 604/509 |
| 7,169,105 B2 * | 1/2007 | Iwasaka et al. | 600/140 |
| 2005/0182387 A1 * | 8/2005 | Webler | 604/527 |
| 2006/0036132 A1 | 2/2006 | Renner et al. | 600/160 |

FOREIGN PATENT DOCUMENTS

| | | |
|---|---|---|
| DE | 10 2004 008 458 | 8/2005 |
| WO | WO 2005/077254 | 2/2005 |

OTHER PUBLICATIONS

STORZ catalogue ART-TEL 4; Hopkins II Telescopes; Apr. 1997; 1 page.

* cited by examiner

ENDOSCOPE

CROSS REFERENCE TO RELATED APPLICATION

The present application claims priority of German patent application No. 10 2005 051 209.7 filed on Oct. 18, 2005.

BACKGROUND OF THE INVENTION

The invention generally relates to endoscopes.

Such endoscopes are used, for example, in minimally invasive interventions in arthroscopy, laparoscopy and thoracoscopy, for inguinal hernias, and in operations on the joints and spinal column. The endoscopes help the operating surgeon carry out the operation, by providing a range of view as large as possible of the operating site.

During such operations, these instruments have to be able to be introduced into the operating site through extremely small access routes. This requires the use of instruments that are as slender as possible.

Such an endoscope has an elongate shaft. This elongate shaft comprises two tubes pushed one inside the other. The diameter of the inner tube is chosen such that it is radially spaced apart from the outer tube. A channel is thereby formed between the inner and outer tubes. This channel is used to receive a light guide, which is formed by a large number of glass fibers.

A distal end of the shaft is beveled, and a correspondingly worked lens is fitted on distally. This arrangement ensures that the operating site can be seen through the lens at a viewing angle of 30° or 70°, for example, relative to the central longitudinal axis of the endoscope.

The shaft is received with its proximal end in an endoscope head. The inner tube can in this case extend into an internal bushing of the endoscope head. The proximal end of the outer tube of the shaft terminates in the endoscope head in such a way that the channel leads through a hollow space to a light guide connection in the endoscope head.

This light guide connection is arranged in the endoscope head, transverse to the longitudinal axis of the shaft, and has a central opening. Thus, the channel continues uninterrupted from the distal end to the proximal end of the shaft.

By means of a light guide, for example a glass fiber bundle, arranged in the channel, it is therefore possible to guide light through this channel in order to illuminate the operating site.

An eyepiece can also be mounted on the endoscope head so that an operating surgeon is able to comfortably view the operating site through the eyepiece and the shaft. For this purpose, a set of lenses or rod lenses is arranged in the inner tube. Instead of an eyepiece for direct viewing through the endoscope, a video camera can also be provided at the proximal end, and its image signals can be displayed on a monitor.

During an operation, it can happen that the operating surgeon has to change the position of the endoscope in order to be able to view the operating site from another angle. In some circumstances, forces may then act laterally or obliquely on the endoscope shaft, with the result that the shaft bends slightly. The proximal part of the shaft is particularly affected by bending.

It is regarded as being particularly disadvantageous that substantial bending of the shaft can cause the rod lenses to fracture. However, even less substantial bending can be enough to cause the glass fibers in the channel to break. Such damage to the endoscope entails at least a limited function, through weakening of the light guidance. If, in addition, a rod lens were to break, this would render the endoscope completely unusable. Damage of this kind is a particularly serious disadvantage during an operation.

From document DE 103 07 903 A1, a method for mounting an endoscope as well as such an endoscope is known. The shaft of this known endoscope comprises an outer tube in which an inner tube for receiving the imaging optics is arranged. The light guides arranged between the inner and outer tubes are received in a flexible host.

In document U.S. Pat. No. 4,790,295, there is described an endoscope, the shaft of which comprises an outer tube. An inner tube is arranged inside the outer tube for leading through forceps. Further, a short intermediate tube serving as a lens frame, is received within the outer tube distally. Image guiding elements are arranged in the lens frame. The light guides are arranged between the inner and the outer tubes. The intermediate tube configured as lens frame does not surround the inner tube.

From document DE 10 2004 008 458 A1, a method for fixing glass fibers in an endoscope is known. The shaft of this endoscope comprises an outer tube. An inner tube configured as optics tube is arranged within the outer tube, in which inner tube image guiding elements are arranged. Glass fiber bundles for guiding light extend between the both tubes.

Finally, from document DE 199 28 289 A1, an endoscope is known the shaft of which comprises an outer tube. Two inner tubes, namely a working tube for irrigation liquids and an optics tube for receiving image guiding elements, are arranged within the outer tube. Light guide fibers for guiding light are arranged between the optics tube, the working tube and the outer tube.

With all known endoscopes described above, the disadvantage continues to exist that the glass fibers of the light guide or lenses are not sufficiently protected against fracture.

SUMMARY OF THE INVENTION

An object of the present invention is therefore to take an endoscope of the type mentioned at the outset and to develop it in such a way that the danger of the lenses or of the light guide breaking during use of the endoscope is at least reduced.

According to an aspect of the invention, an endoscope is provided, comprising a shaft having a distal end and a proximal end and defining a longitudinal direction. The shaft has an outer tube and an inner tube, the inner tube extending inside the outer tube, the outer tube and the inner tube being radially spaced apart from one another such that a channel for receiving a light guide is formed between the outer tube and the inner tube, the channel extending in the longitudinal direction. The shaft further has an intermediate tube having flexural strength which is arranged between the outer tube and the inner tube, the intermediate tube at least partially surrounding the inner tube.

The shaft is advantageously strengthened by the intermediate tube having flexural strength that extends through the shaft between the outer tube and the inner tube. Material strengthening of this kind leads to increased stability of the shaft. For this reason, forces acting laterally or obliquely on the shaft no longer cause bending of the shaft, or they do so only to a lesser extent. The shaft that has been strengthened in this way performs two protective functions. On the one hand, rod lenses located in the shaft are protected against being broken off or broken into pieces by bending forces. On the other hand, a light guide extending in the channel between the inner tube and the outer tube is also protected against bending forces. Damage to the light guide is avoided by this means.

Since the intermediate tube is arranged between the inner and outer tubes, an increase in the external diameter of the shaft is advantageously avoided.

In a preferred embodiment, the intermediate tube is shorter than the outer tube or the inner tube.

This measure has the advantage that, by means of a shorter intermediate tube, a similarly strengthened shaft can be produced which is strengthened at particularly stressed areas of the endoscope, but which uses up less material compared to an unshortened intermediate tube. The shortened intermediate tube also facilitates the assembly of an endoscope shaft, since any catching or jamming of the intermediate tube can be more easily corrected during assembly, by virtue of the better handling of shorter parts.

In another preferred embodiment of the invention, the intermediate tube is arranged in a proximal area of the shaft.

This measure has the advantage that the intermediate tube provided for strengthening purposes is arranged in that area of the shaft which is most exposed to stresses caused by laterally and obliquely acting forces and which is most inclined to bend. As has been mentioned above, the stresses that arise can lead to the light guide or rod lenses breaking, but this can now be avoided. A strengthening tube arranged at the proximal end makes bending of the shaft difficult or impossible in this area and therefore effectively protects said elements from damage.

In another preferred embodiment, the intermediate tube has an axial slit.

This measure has the advantage that the intermediate tube can be more easily inserted between the two other tubes during assembly of the shaft. By means of radial compression of the slit intermediate tube, wedging or jamming of the intermediate tube during its insertion is made virtually impossible or can be easily corrected. If the intermediate tube becomes stuck during its insertion, light compression of the intermediate tube allows this resistance to be overcome, and the intermediate tube can be pushed onward past the obstacle. This is possible until complete insertion of the intermediate tube, thereby making assembly of the shaft considerably easier.

In addition, this measure has the advantage that, with suitably chosen dimensions, the intermediate tube fits very snugly against the outer tube from the inside. During practical application of the endoscope, this ensures that the intermediate tube cannot move to and fro between the outer and inner tubes.

In another preferred embodiment of the invention, the intermediate tube is beveled at its proximal end.

This measure has the advantage that an area in the proximal end of the shaft remains free of the intermediate tube. The introduction of the light guide into the channel, i.e. into the space between inner tube and outer tube, can be done without causing stresses or without any kinking on the intermediate tube. In this way, it is possible to avoid the light guide resting on the proximal end of the intermediate tube or becoming kinked and thereby running the risk of breaking off at this end.

In another preferred embodiment of the invention, the shaft, viewed radially from the inside outward, comprises the inner tube, the intermediate tube, the channel, and the outer tube.

This measure has the advantage that the inner tube is additionally strengthened by this arrangement of the tubes. This increases the stability of the shaft, and bending of the shaft occurs only if a correspondingly increased bending force acts on it. Thus, the rod lenses arranged in the inner tube are on the whole better protected by the shaft. The likelihood of the rod lenses breaking off or breaking into pieces is therefore very much less than in a shaft that is not strengthened.

In another preferred embodiment of the invention, the shaft, viewed radially from the inside outward, comprises the inner tube, the channel, the intermediate tube, and the outer tube.

The advantage of this arrangement of the tubes is that the rod lenses in the inner tube and also the channel for receiving the light guide are better protected by the strengthening of the shaft. Bending of the shaft only occurs at higher forces than in the case of an unprotected shaft. As has already been mentioned, this prevents the rod lenses from breaking off or breaking into pieces and also avoids the light guide being damaged by bending of the shaft.

In another preferred embodiment of the invention, the intermediate tube is designed, in terms of its length and wall thickness, such that the intermediate tube only fills a space between outer tube and inner tube that is left free from the light guide.

This measure has the advantage of ensuring that, when the intermediate tube is introduced into the channel, the space for the light guide in the channel is left unchanged in terms of its dimensions. Consequently, it is also true that the dimensions of a light guide also remain unchanged. In this way, unchanged light guide properties are ensured along the entire channel.

This results in light being guided in a manner completely uninfluenced by the intermediate tube and, consequently, in a uniform and constant illumination of the operating site. When performing an operation, an operating surgeon is thus provided with a strengthened and more stable endoscope having the same light guidance properties as in an unstrengthened endoscope.

In another preferred embodiment of the invention, a partially circumferential segment is pushed distally onto the inner tube and is arranged substantially between the outer tube and the inner tube.

This measure has the advantage that a spacer is fitted in an area between the inner tube and the outer tube. This ensures that, in practical use, the intermediate tube maintains its position at the distal end. The rod lenses are thus protected from slipping as a result of bending of the shaft. This ensures that the optical properties of the endoscope are maintained during practical application.

In another preferred embodiment of the invention, the partially circumferential segment comprises a lens.

This measure has the advantage that the distally arranged lens of the endoscope can be exchanged together with an exchangeable segment arranged at the distal end of the shaft. Since the distal part of this lens is exposed to particular stresses and wear when positioned at the operating site, it is advantageous to replace this lens after a certain period of time and in this way to bring the endoscope into working order again. It is therefore not necessary to replace the complete endoscope after this one lens has become worn. Reducing the need for replacement to parts that have become worn signifies a saving in terms of material and costs.

In another preferred embodiment, the segment is beveled at its distal end.

This measure has the advantage that, in the distal area of the shaft, the light guide can be arranged around the partially circumferential segment. This allows the light outlet to be positioned obliquely with respect to the central longitudinal axis of the endoscope. The operating site is then illuminated at a corresponding angle. In combination with a correspondingly beveled lens, this extends the operating surgeon's view of the operating site.

In another preferred embodiment, the light guide is a glass fiber bundle.

This measure has the advantage of ensuring acceptable illumination of the operating site even if a small number of glass fibers in this bundle fail.

It will be appreciated that the aforementioned features and those still to be explained below can be used not only in the respectively cited combination, but also in other combinations or singly, without departing from the scope of the present invention.

BRIEF DESCRIPTION OF THE DRAWINGS

The invention is described and explained in greater detail below on the basis of a selected illustrative embodiment and with reference to the attached drawings, in which.

DETAILED DESCRIPTION OF A PREFERRED EXEMPLARY EMBODIMENT

Figure 1:
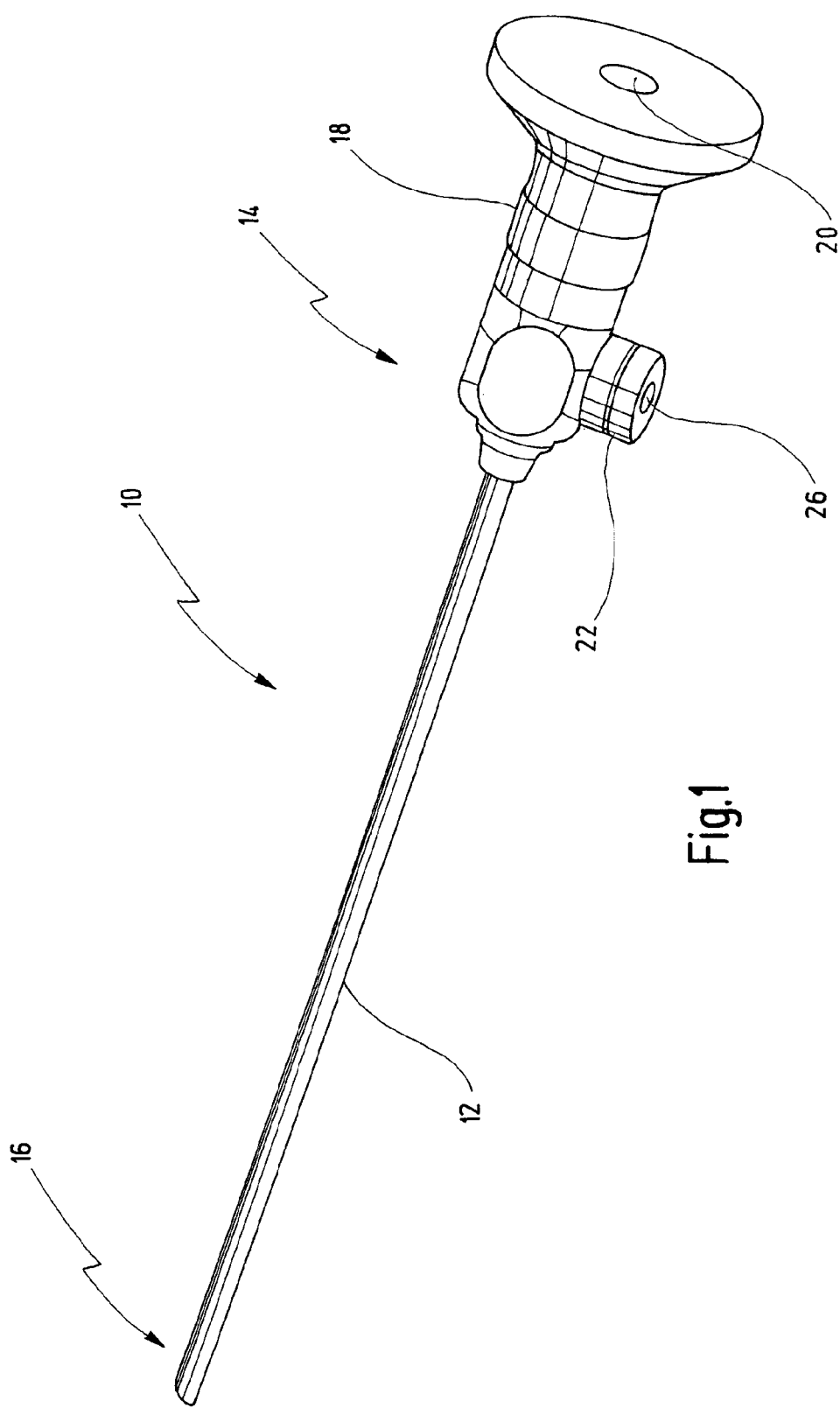
FIG. 1 shows a perspective view of an endoscope according to the invention.

In FIG. 1, an endoscope is designated in its entirety by reference number 10.

This endoscope 10 comprises a shaft 12 with a proximal end 14 and a distal end 16.

The shaft 12 is also received with its proximal end 14 in an endoscope head 18.

Figure 2:
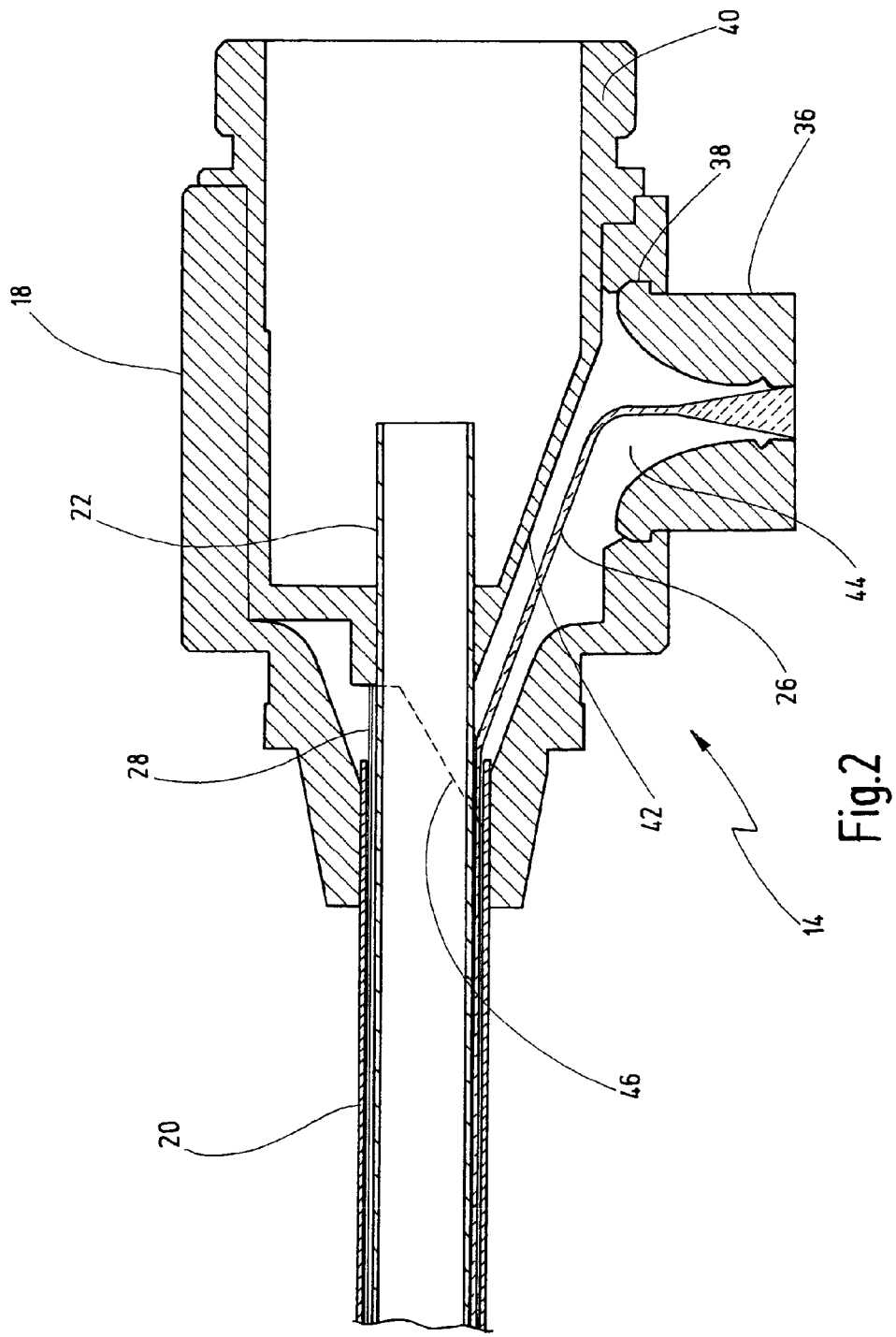
FIG. 2 shows a cross section through an endoscope according to the invention, with an endoscope head and with part of the shaft.
Figure 3:
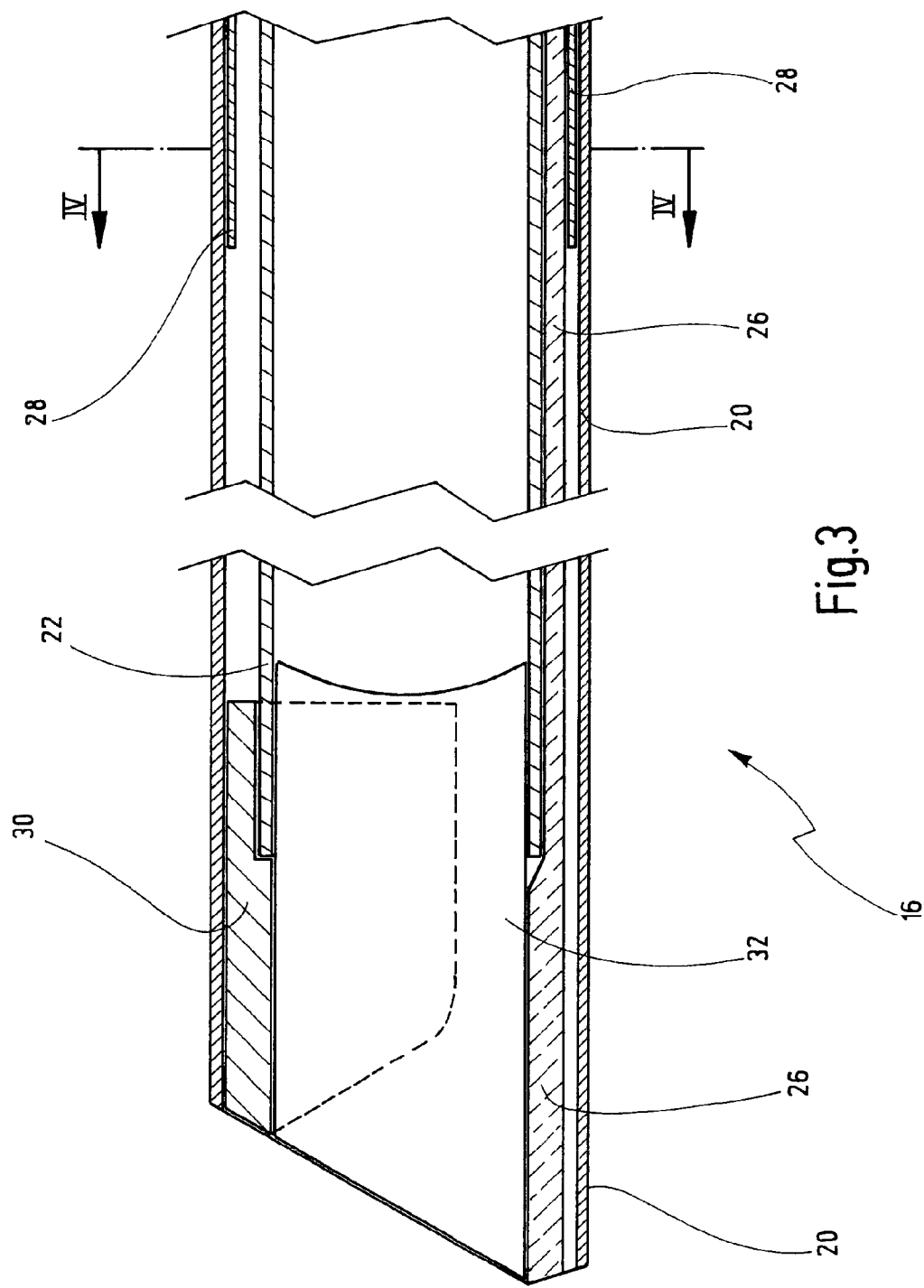
FIG. 3 shows an interrupted and enlarged view of the distal end of a shaft.
Figure 4:
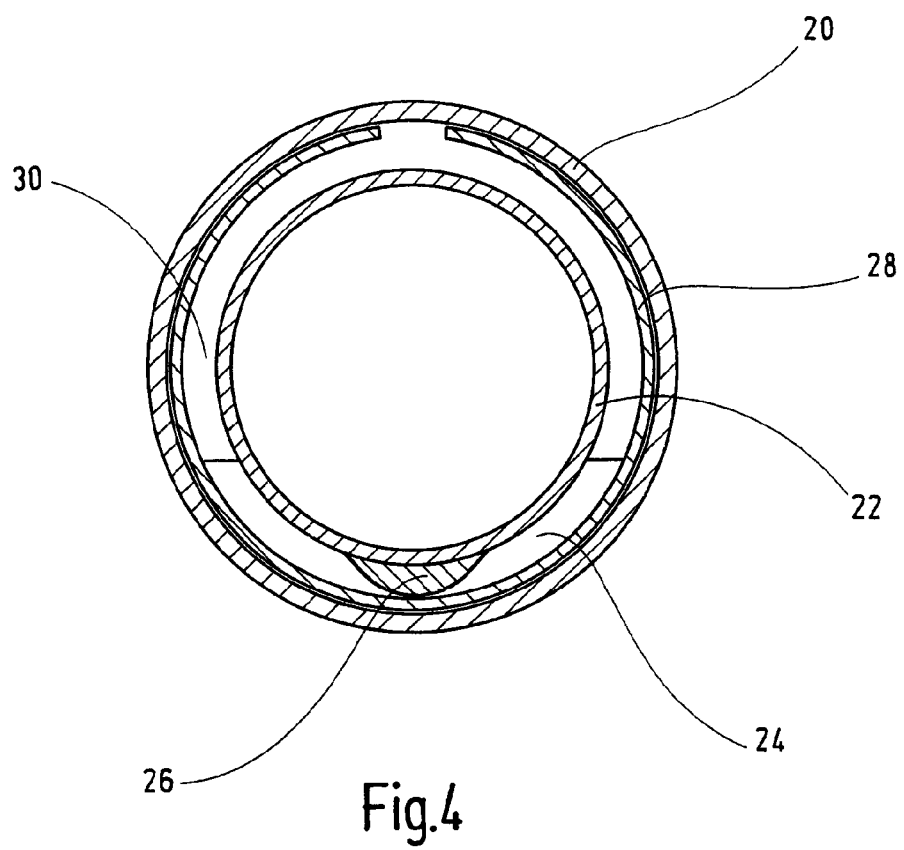
FIG. 4 shows a cross section along the line IV-IV in FIG. 3.

In the schematic view in FIG. 2, and also in FIGS. 3 and 4, it will be seen that the shaft 12 is made up of several parts.

The shaft 12 has an outer tube 20. An inner tube 22 of smaller diameter extends inside this outer tube 20. These two tubes 20 and 22 are spaced apart from one another in such a way that they together form a channel 24. FIG. 4 illustrates how this channel 24 provides sufficient space for a light guide 26 inserted in it.

Moreover, the outer tube 20 and the inner tube 22 are spaced apart from one another in such a way that, besides receiving the light guide 26, the channel 24 has additional free space which, in the endoscope 10 according to the invention, is made use of by insertion of an intermediate tube 28.

As is shown in FIG. 2, the intermediate tube 28 is shorter than the outer tube 20 and inner tube 22. Moreover, the intermediate tube 28 is arranged in a proximal area of the shaft 12 susceptible to bending forces. It additionally has an axial slit, which allows the intermediate tube 28 to be radially compressed. FIG. 2 also shows, with the broken lines, that the intermediate tube 28 is beveled at its proximal end.

In the preferred embodiment of the endoscope 10 shown in FIG. 2, the intermediate tube 28 is arranged in the shaft 12 in such a way that said shaft 12, viewed radially from the inside outward, comprises the inner tube 22, the channel 24, the intermediate tube 28, and the outer tube 20.

In this arrangement, the intermediate tube 28 rests snugly on the inside wall of the outer tube 20.

However, another embodiment (not shown here) is also conceivable in which the shaft 12, viewed radially from the inside outward, comprises the inner tube 22, the intermediate tube 28, the channel 24, and then the outer tube 20.

In this arrangement, the intermediate tube 28 rests tightly on the outside wall of the inner tube 20, such that the channel 24 for the light guide 26 is maintained.

It is important overall, for the function of the endoscope 10, that the intermediate tube 28 only fills a space between outer tube 20 and inner tube 22 that is left free from the light guide 26.

The function of the intermediate tube 28 is described further below.

As can be seen from FIGS. 1 and 3, the shaft 12 is beveled at its distal end 16. FIG. 3 also shows that a segment 30 is provided in the distal end 16 of the shaft 12. This segment 30 has a bevel at its distal end. The segment 30 is used to support a lens 32. The lens 32 is shaped to correspond to the bevel of the distal end 16 and, by means of its refractive power, provides the endoscope 10 with an altered direction of viewing and an extended field of vision.

The segment 30 has a length of approximately 1 to 2 cm, for example. It has roughly the shape of a half-tube and extends in a partial circumference about the inner tube 22, its dimensions allowing it to be fitted into the outer tube 20. In this way, it fills the space between the two tubes 20 and 22 and sits between them with a form fit.

On its inside wall, the segment 30 has a shoulder which is configured such that the segment 30 can be pushed to fit onto the inner tube 22 and come to lie thereon. The depth of insertion of the segment 30 into the outer tube 20 is limited by this means.

The shape of the segment 30 is adapted to its functions. On the one hand, the segment 30 serves as a spacer between the outer tube 20 and the inner tube 22, and, on the other hand, it serves as a fixture for the lens 32.

Depending on the intended application of the endoscope 10, it is possible to set viewing angles of 30° or 70°, for example, relative to the central longitudinal axis of the endoscope 10.

The endoscope 10 also comprises the endoscope head 18.

This endoscope head 18 is also made up of several parts. FIG. 1 shows it is provided at the proximal end with an eyepiece 34 through which an operating surgeon, when performing an endoscopic intervention, is able to inspect an operating site that is to be examined.

It is also conceivable, however, to attach a video camera to the endoscope head 18, and to transmit recorded image signals to a monitor or to digitalize them and analyze them by computer.

The endoscope head 18 moreover comprises a light guide connection 36. As can be seen from FIG. 2, this light guide connection 36 is inserted from the inside into a socket 38. The light guide connection 36 has an opening. The light guide 26 is received in this opening. To make the illustration clearer, the opening and the light guide 26 have been shown enlarged in the area of the outlet of said opening.

A support element 40 is also arranged in the endoscope head 18. In FIG. 2, this support element 40 is shown as a bushing that has an opening at its base.

At the proximal end, the support element 40 has a shoulder via which it bears with a form fit, as an insert, in the endoscope head 18. The endoscope head 18 is thereby proximally sealed.

In the distal direction, the support element 40 has a narrowing area 42 that extends to the opening in the base. With this opening, the support element 40 receives the inner tube 22 in the endoscope head 18.

Overall, the support element 40 is configured by the narrowing area 42 in such a way that a hollow space 44 forms in the endoscope head 18. This hollow space 44 is linked proximally to the channel 24 and widens the latter into the endoscope head 18. The light guide 26 is routed to the light guide connection 36 through this hollow space 44.

As has already been described above, and as can be seen from FIGS. 2 to 4, an intermediate tube 28 is arranged between the outer tube 20 and inner tube 22.

This intermediate tube 28 sits with its proximal end on the support element 40. It has a bevel 46 at its proximal end, so that it sits on the support element 40 only via a reduced tube edge.

This configuration of the intermediate tube 28 is advantageous when the light guide 26 coming from the light guide connection 36 is routed through the hollow space 44 and into the channel 24 to the distal end 16 of the shaft 12.

A glass fiber bundle is particularly suitable as light guide 26. Such a glass fiber bundle is also preferably used as the light guide 26 in the invention described and illustrated here.

The intermediate tube 28 also has a slit extending completely through the intermediate tube 28 in an orientation parallel to the longitudinal axis. The intermediate tube 28 is in this case preferably inserted into the shaft 12 in such a way that the slit comes to lie diametrically opposite the light guide 26, as can be seen from FIG. 4.

If the intermediate tube 28 were to become jammed or caught in the outer tube 20 during assembly of the shaft 12, the intermediate tube 28 could be lightly compressed, by virtue of the slit, and then pushed onward past the obstruction.

It will be appreciated that the intermediate tube is advantageously made of a material with a high flexural strength, in particular of steel that is used for medical instruments of this kind, or of metal alloys, for example Monel, Phynox (cobalt alloy).

Overall, this results in the endoscope 10 having a stable shaft 12 that is preferably strengthened at those locations which, during practical use of the endoscope 10, are particularly subjected to laterally or obliquely acting forces.

What is claimed is:

1. An endoscope comprising:
    a shaft having a distal end and a proximal end and defining a longitudinal direction,
    said shaft having an outer tube and an inner tube, said inner tube extending inside said outer tube, the proximal end comprising an endoscope head having a support element therein,
    said outer tube and said inner tube being radially spaced apart from one another such that a channel for receiving a light guide is formed between said outer tube and said inner tube, said channel extending in said longitudinal direction, and
    said shaft further having an intermediate tube having an axial slit extending in the longitudinal direction of the intermediate tube, the axial slit extending over the entire length of the intermediate tube, the intermediate tube being made of steel or of a metal alloy having flexural strength which strengthens said shaft against bending forces, said intermediate tube being arranged between said outer tube and said inner tube, said intermediate tube at least partially surrounding said inner tube, said intermediate tube, due to the axial slit being compressible in order to facilitate assembly of the shaft and fitting snugly against the outer tube from the inside of the outer tube,
    wherein said shaft viewed radially from the inside outward, comprises said inner tube, said channel, said intermediate tube, and said outer tube,
    wherein a partially circumferential segment is pushed distally onto said inner tube and is arranged substantially between said outer tube and said inner tube, and
    wherein said partially circumferential segment is beveled at a distal end of said circumferential segment,
    wherein the intermediate tube has a bevel at its proximal end and arranged in a proximal area of said shaft such that said bevel sits on said support element.

2. The endoscope of claim 1, wherein said intermediate tube is shorter than said outer tube.

3. The endoscope of claim 1, wherein said intermediate tube is shorter than said inner tube.

4. The endoscope of claim 1, wherein said intermediate tube is configured, in terms of its length and wall thickness, such that said intermediate tube only fills a space between said outer tube and said inner tube that is left free from said light guide.

5. The endoscope of claim 1, wherein said partially circumferential segment comprises a lens.

6. The endoscope of claim 1, wherein said light guide is a glass fiber bundle.

* * * * *